United States Patent
Fawcett et al.

(10) Patent No.: US 9,829,419 B2
(45) Date of Patent: Nov. 28, 2017

(54) METHOD FOR ASSESSING HAIR FIBERS

(71) Applicant: Conopco, Inc., Englewood Cliffs, NJ (US)

(72) Inventors: Sandra Anne Fawcett, Southport (GB); Geraldine Griffith, Chester (GB); Sophia Paraskevi Clare Moghadam (nee Papapavlou), Bromborough (GB); Claire Louise Richards, Wrexham (GB)

(73) Assignee: Conopco, Inc., Englewood Cliffs, NJ (US)

( * ) Notice: Subject to any disclaimer, the term of this patent is extended or adjusted under 35 U.S.C. 154(b) by 115 days.

(21) Appl. No.: 14/762,111

(22) PCT Filed: Dec. 20, 2013

(86) PCT No.: PCT/EP2013/077662
§ 371 (c)(1),
(2) Date: Jul. 20, 2015

(87) PCT Pub. No.: WO2014/117907
PCT Pub. Date: Aug. 7, 2014

(65) Prior Publication Data
US 2015/0355063 A1 Dec. 10, 2015

(30) Foreign Application Priority Data

Feb. 1, 2013 (EP) .................................... 13153649

(51) Int. Cl.
*G01N 3/08* (2006.01)
*G01N 1/28* (2006.01)
(Continued)

(52) U.S. Cl.
CPC ................. *G01N 3/08* (2013.01); *G01N 1/28* (2013.01); *G01N 19/02* (2013.01); *G01N 3/14* (2013.01);
(Continued)

(58) Field of Classification Search
CPC ............ G01N 3/08; G01N 1/28; G01N 19/02; G01N 2203/028; G01N 2203/0089
(Continued)

(56) References Cited

U.S. PATENT DOCUMENTS 1,458,529 A * 6/1923 Hill .................... G01N 11/10
73/150 R
3,921,443 A * 11/1975 Yates .................... G01N 3/066
73/160
(Continued)

FOREIGN PATENT DOCUMENTS

DE 19924741 A1 12/2000
JP 56-027652 A2 3/1981
(Continued)

OTHER PUBLICATIONS

Vaynberg et al. "The Aqualong SLT: A novel device for measuring hair stiffness and lubricity". Journal of Cosmetic Science, vol. 60, pp. 135-141; Mar./Apr. 2009. Access [Online] Jan. 8, 2017 <http://citeseerx.ist.psu.edu/viewdoc/download?doi=10.1.1.845.6172&rep=rep1&type=pdf>.*
(Continued)

*Primary Examiner* — Jonathan Dunlap
(74) *Attorney, Agent, or Firm* — Greenberg Traurig, LLP

(57) ABSTRACT

A method for assessing the state of hair by releasably engaging a first end of hair fibers with a holder which so that an opposite, second end of said hair fibers hangs free and
(Continued)

Figure 1:
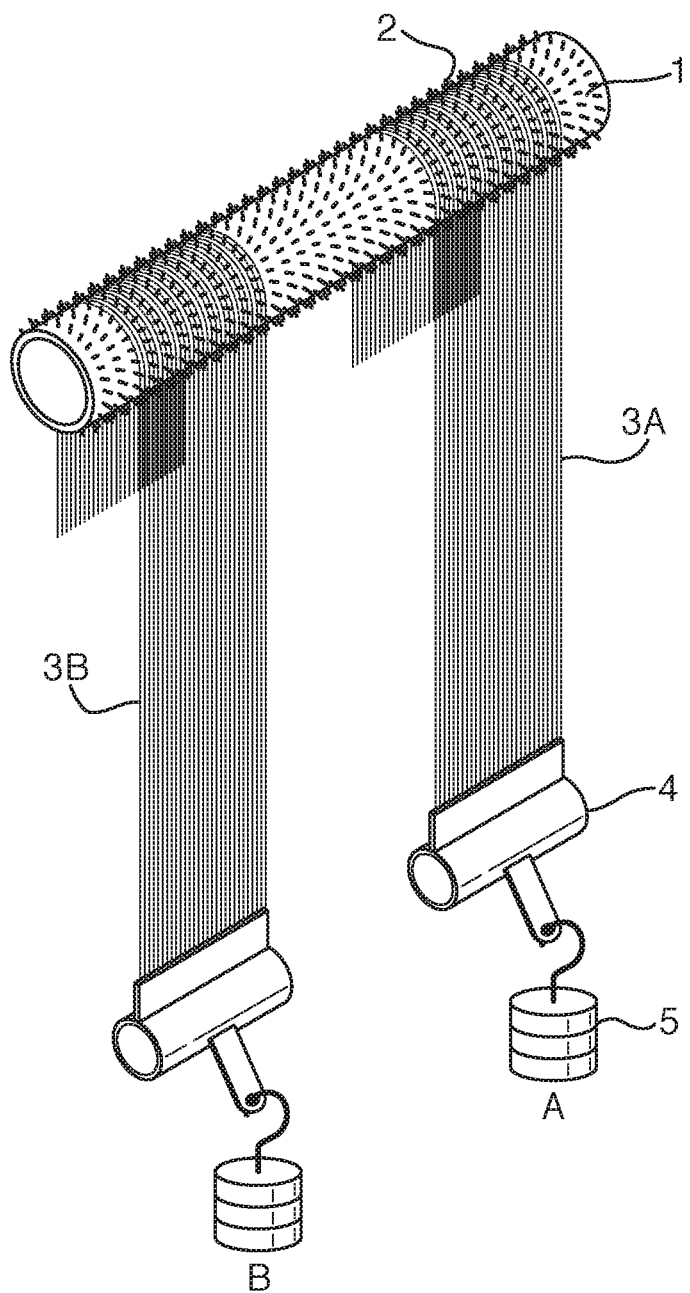

applying sufficient force to the second end of the hair fibers such that the hair fibers at the first end are pulled from the holder.

6 Claims, 2 Drawing Sheets

(51) Int. Cl.
    *G01N 19/02*     (2006.01)
    *G01N 3/14*     (2006.01)

(52) U.S. Cl.
    CPC ............... *G01N 2203/0089* (2013.01); *G01N 2203/028* (2013.01)

(58) Field of Classification Search
    USPC ................. 73/150 A, 150 R, 159, 160, 9
    See application file for complete search history.

(56) References Cited

U.S. PATENT DOCUMENTS

| | | | | |
|---|---|---|---|---|
| 3,946,606 | A * | 3/1976 | Abrioux | G01L 5/00 |
| | | | | 132/219 |
| 4,061,022 | A | 12/1977 | Yates | |
| 4,167,869 | A * | 9/1979 | Gikas | A45D 24/10 |
| | | | | 132/219 |
| 4,628,742 | A | 12/1986 | Golding | |
| 4,628,747 | A * | 12/1986 | Weitz | G01L 5/103 |
| | | | | 254/134.3 FT |
| 4,665,741 | A | 5/1987 | Kabacoff | |
| 6,817,222 | B2 * | 11/2004 | Day | G01N 19/02 |
| | | | | 73/9 |
| 7,472,577 | B2 * | 1/2009 | Shibuichi | A61B 7/00 |
| | | | | 73/9 |
| RE41,046 | E | 12/2009 | Cohen | |
| 7,928,739 | B2 * | 4/2011 | Sherman | G01N 22/04 |
| | | | | 324/640 |
| 8,151,624 | B2 * | 4/2012 | Sherman | G01N 19/02 |
| | | | | 73/9 |
| 8,429,963 | B2 | 4/2013 | Yagnik | |
| 8,833,137 | B2 * | 9/2014 | Yagnik | A61K 8/342 |
| | | | | 73/159 |
| 2003/0233861 | A1 * | 12/2003 | Woolston | G01N 19/02 |
| | | | | 73/9 |
| 2006/0184068 | A1 | 8/2006 | Shibuichi et al. | |
| 2007/0028680 | A1 * | 2/2007 | Brouwers | G01N 19/04 |
| | | | | 73/150 A |
| 2009/0071228 | A1 * | 3/2009 | Sherman | G01N 19/02 |
| | | | | 73/9 |
| 2013/0213127 | A1 * | 8/2013 | Tynan, Jr. et al. | G01N 19/04 |
| | | | | 73/150 A |
| 2015/0260635 | A1 * | 9/2015 | White | G01N 3/00 |
| | | | | 73/150 A |
| 2016/0061809 | A1 * | 3/2016 | Meinert | G01N 3/08 |
| | | | | 73/159 |

FOREIGN PATENT DOCUMENTS

| | | |
|---|---|---|
| JP | 56-027652 A2 | 3/1981 |
| JP | 56-094260 A2 | 7/1981 |
| JP | 63163143 | 7/1988 |
| JP | 03152439 A * | 6/1991 |
| JP | 04098146 A * | 3/1992 |
| WO | WO2007108318 A1 | 9/2007 |
| WO | WO2012173963 A1 | 12/2012 |

OTHER PUBLICATIONS

Newman et al. "A quantitative characterization of combing force". Journal of the Society of Cosmetic Chemists, vol. 24, Dec. 9, 1973, pp. 773-782. Accessed [Online] Apr. 14, 2017. <http://citeseerx.ist.psu.edu/viewdoc/summary?doi=10.1.1.603.1012>.*
Ishii, "Objective and Instrumental Methods for Evaluation of Hair Care Product Efficacy and Substantiation of Claims", Hair and Hair Care, 1997, Chap 10, pp. 267-269, and 296-297.
Ishii, Objective and Instrumental Methods for Evaluation of Hair Care Product Efficacy and Substantiation of Claims, Hair and Hair Care, 1997, 267-269, Chap 10. pp. 1 to 5.
Search Report in EP13153649 dated Jul. 30, 2013. pp. 6 to 7.
Search Report in PCTEP2013077662 dated Apr. 2, 2014. pp. 8 to 10.
Written Opinion in EP13153649 dated Jul. 30, 2013. pp. 11 to 14.
Written Opinion in PCTEP2013077662 dated Apr. 2, 2014. pp. 15 to 18.

* cited by examiner

METHOD FOR ASSESSING HAIR FIBERS

The present invention relates to a method for assessing the state of hair fibres, the efficacy of conditioning compositions on said fibres and methods for assessing and comparing the efficacy of conditioning compositions.

WO2012/173963A1 discloses using mechanized strategies to fabricate test samples as well as strategies for selecting sample substrates.

JP S56 94260 (Sharp KK) discloses a method for assessing the state of hair where the breaking point is measured.

JP S56 27652 (Sharp KK) discloses a similar method where the hair is clamped on a capillary tube.

Despite the prior art there remains a need for improved methods for demonstrating the condition of hair fibres.

Accordingly, and in a first aspect, there is provided a method for assessing the state of hair by releasably engaging a first end of hair fibres with a holder so that an opposite, second end of said hair fibres hangs free and applying sufficient force to the second end of the hair fibres such that the hair fibres at the first end are pulled from the holder.

Preferably, the holder comprises bristles or tines and the hair fibres are pulled through the bristles or tines as force is applied to the second end.

Preferably, the force is applied in a direction away from the holder.

Preferably, the method comprises recording the force applied for the hair switch. Preferably, the method further comprises comparing the force applied to one hair switch with the force applied to another hair switch required to achieve the same or comparable result.

Preferably, the force is sufficient to pull the hair completely from the hair fibre. Preferably, the force is the minimum force required to pull all the fibres from the holder within a minimum period of one minute from first application of force.

Preferably, the force is applied by attaching mass to the second end of the hair fibres.

The method provides an easily demonstrable approach to assessing the state of the hair, more preferably, the state of tanglement of the hair fibres.

Preferably, the force is applied in a progressive manner, i.e. the first force applied is preferably insufficient to pull the hair fibres from the holder but further or greater force is applied until a point is reached when the hair fibres are pulled from the holder at a predetermined rate. Preferably, the rate is easily discernable to the eye.

Preferably, a clip is attached to the second end of hair fibres and weights are added progressively to the clip.

Preferably, the holder is a brush or comb. More preferably, the holder comprises bristles or tines which extend in a direction away from the direction of applied force. Preferably, the bristles or tines extend in a direction opposite to that of the gravitational force.

Preferably, the hair fibres are in the form of hair switches and preferably are from 1 to 5 g switches, more preferably 1.5 to 3 g switches.

Preferably the switches are from 10 to 50 cm in length, more preferably from 15 to 30 cm in length and most preferably from 20 to 28 cm in length.

Should the hair be significantly tangled then the force required to pull the hair fibres from the holder is greater than for not significantly tangled hair. Further, where there is a comparison between two or more hair switches of differing degrees of tanglement one will pull through the hair more easily, or with less mass than the other. This would thus provide a purposeful demonstration of the efficacy of one conditioning treatment over another.

Preferably, the hair is wetted immediately prior to attaching to the holder. By immediately prior means such a length of time that the hair does not significantly dry. Preferably, this means from 0 to 20 minutes, more preferably from 0 to 10 minutes, especially preferably from 0 to 1 minute and most preferably from 0 to 30 seconds.

By wetted is meant having water applied thereto. Preferably, the hair is rinsed immediately prior to attaching to the holder.

More preferably, the hair is rinsed for from 2 to 20 seconds, especially preferably from 4 to 12 seconds immediately prior to attaching to the holder.

Preferably, the hair is treated with a conditioning composition before the hair is wetted, preferably rinsed, and attached to the holder. This allows the operator to assess the efficacy of the conditioning composition by recording the mass required to pull the hair fibres from the holder.

Preferably, the hair is treated with a conditioning composition and then rinsed immediately prior to attaching to the holder.

Preferably the applied conditioning composition is a rinse-off conditioning composition.

In a second aspect there is provided a method for measuring the conditioning efficacy of a conditioning composition by applying a conditioning composition to hair, wetting the hair, and releasably engaging the hair with the holder and then measuring the force required to pull the hair from the holder.

Preferably, the time taken to pull the hair from the holder is sufficiently short for an easy record to be made but not so short that the hair is pulled immediately from the holder.

In a third aspect there is provided a method for comparing the conditioning efficacy of at least two conditioning compositions by performing the method of the second aspect on the treated hair samples.

Preferably, the method of comparing the conditioning efficacy of at least two conditioning compositions is conducted simultaneously on the treated hair samples.

This allows the operator to immediately determine superiority of one composition over another without the need to measure the mass involved or the time taken to pull the hair through the holder.

Preferably, the first mass attached to the hair fibres is of insufficient weight to pull the hair fibres from the holder and mass is sequentially added in a manner which permits differentiation between the two sets of hair fibres. In other words, identical mass is attached to each set of hair fibres simultaneously until one of the sets of hair fibres is pulled from the holder and the other is maintained attached to the holder. This would demonstrate superiority of the conditioning efficacy of the composition treating the former set of hair fibres over that applied to the latter.

FIG. 1 shows a cylindrical brush (1) with radially extending bristles (2). Two hair switches (3A and 3B) are attached over the brush (1) such that they hang loose. At the loose end of each of the switches is a clip (4) with weight (5) depending therefrom.

Figure 2:
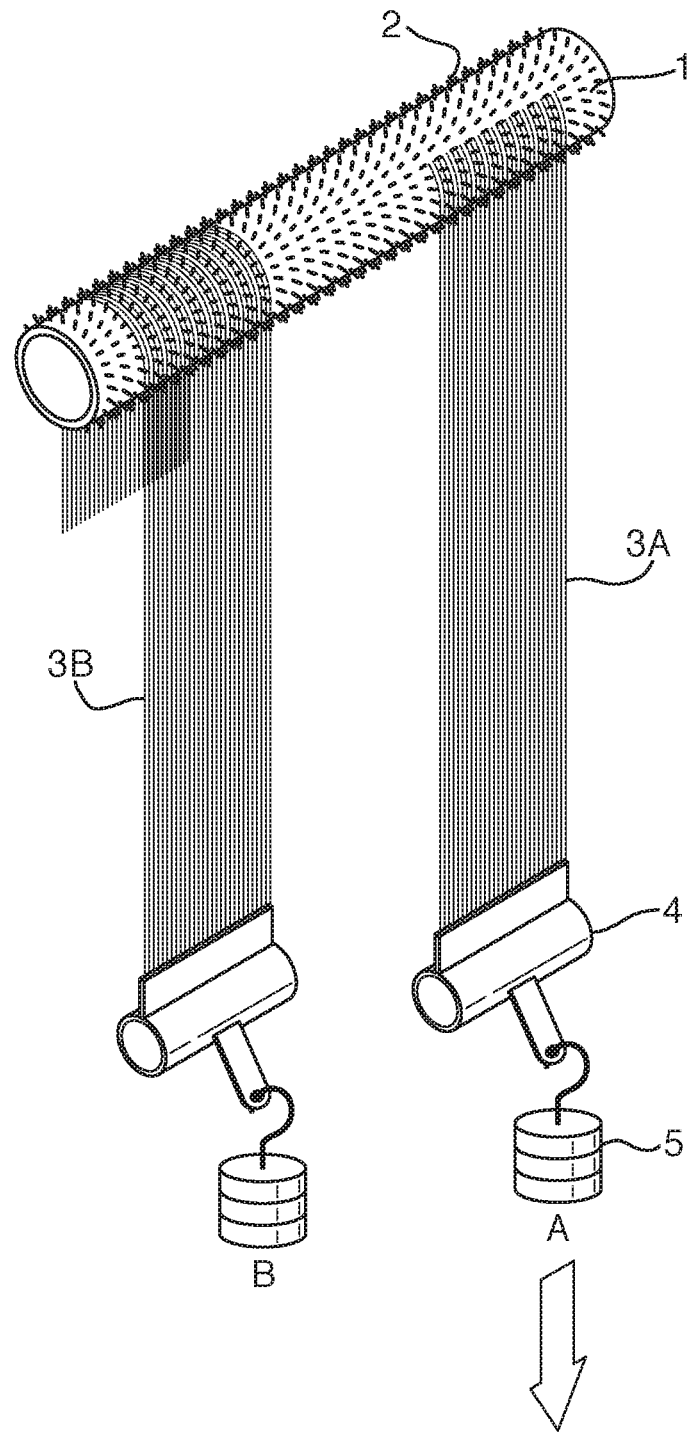

FIG. 2 shows a pair of switches as described in FIG. 1. Switch A is pulled more easily from the cylindrical brush than switch B.

EXAMPLE 1

A hair switch is treated with a conditioning composition and then rinsed for 10 seconds.

One end of the switch is attached to a cylindrical brush and the other end is left to hang freely. A bulldog clip is attached to the free hanging end of the hair fibres and a weight attached to the clip. Further weights are added to the clip until the hair switch is pulled from the brush. The switch is then pulled from the brush and falls freely. Weights are added in a manner such that the minimum weight added required to pull the switch from the brush can be recoded.

EXAMPLE 2

The experiment of example 1 is repeated but with two switches treated with different conditioning compositions and a comb is used instead of a brush.

The two switches are conditioned and then rinsed for 10 seconds.

Equal weight is attached to the clips of each fibre simultaneously until sufficient weight is added to one that the switch is pulled from the comb.

The switch which is pulled from the comb more easily is considered the least tangled and so the best conditioned.

The invention claimed is:

1. A method, comprising:
    i) treating a first switch of hair fibres with a conditioning composition;
    ii) wetting, after step (i), the first switch of hair fibres;
    iii) attaching, after step (ii), the first switch of hair fibres to a holder by releasably engaging a first end of the first switch of hair fibres with the holder so that an opposite, second end of the first switch of hair fibres hangs free;
    iv) applying a first force to the second end of the first switch of hair fibres such that a first force is insufficient to pull the first switch of hair fibres at the first end from the holder;
    v) applying a plurality of forces to the second end of the first switch of hair fibres, wherein the plurality of forces are progressively increased from a second force that is greater than the first force until a third force which is sufficient to pull the first switch of hair fibres at the first end from the holder, and wherein the second force is smaller than the third force; and
    vi) applying the third force to a second switch of hair fibres to assess a state of hair fibres.

2. The method according to claim 1, wherein the composition is a rinse-off conditioning composition.

3. A method for comparing or demonstrating the conditioning efficacy of at least two conditioning compositions by performing the method of claim 1 on hair fibres treated with the at least two conditioning compositions.

4. The method according to claim 3, wherein the method of claim 1 is conducted simultaneously on the treated hair fibres.

5. The method according to claim 1, wherein the applying the first force comprises attaching a first mass to the second end of the first switch of hair fibres.

6. The method according to claim 1, wherein the applying the plurality of forces comprises attaching a plurality of masses to the second end of the first switch of hair fibres and wherein the second force corresponds to a second mass and the third force corresponds to a third mass.

* * * * *